(12) United States Patent
Braud

(10) Patent No.: US 8,764,629 B2
(45) Date of Patent: Jul. 1, 2014

(54) EXTERNAL PROSTHESIS SYSTEMS

(76) Inventor: Callan Braud, Prairieville, LA (US)

( * ) Notice: Subject to any disclaimer, the term of this patent is extended or adjusted under 35 U.S.C. 154(b) by 312 days.

(21) Appl. No.: 13/037,280

(22) Filed: Feb. 28, 2011

(65) Prior Publication Data

US 2011/0275888 A1 Nov. 10, 2011

Related U.S. Application Data

(60) Provisional application No. 61/331,920, filed on May 6, 2010.

(51) Int. Cl.
*A61F 5/41* (2006.01)
(52) U.S. Cl.
USPC ............................................................ 600/39
(58) Field of Classification Search
CPC ................ A61F 5/41; A61F 2005/411; A61F 2005/414; A61H 19/00
USPC ...................................................... 600/38–41
See application file for complete search history.

(56) References Cited

U.S. PATENT DOCUMENTS

| | | | |
|---|---|---|---|
| 3,920,007 A | 11/1975 | Line et al. | |
| 4,194,502 A | 3/1980 | Eckels | |
| 4,381,000 A * | 4/1983 | Duncan | 600/39 |
| 4,488,541 A * | 12/1984 | Garcia | 600/39 |
| 4,653,484 A | 3/1987 | Cannon | |
| 5,360,390 A | 11/1994 | Maanum | |
| D394,504 S | 5/1998 | Weller et al. | |
| 5,893,827 A * | 4/1999 | Jaquez et al. | 600/38 |
| 6,436,031 B1 | 8/2002 | Salib | |
| 2007/0129600 A1* | 6/2007 | Osbon et al. | 600/38 |

* cited by examiner

*Primary Examiner* — Christine Matthews
(74) *Attorney, Agent, or Firm* — RG Patent Consulting, LLC; Rachel Gilboy

(57) ABSTRACT

A prosthetic device for supporting a flaccid penis during intercourse comprising an oval shaped base having a through-hole, an elongated support platform member having an upper side and a lower side, an adjustable waist-strap, a first adjustable leg strap, and a second adjustable leg strap. The upper side of the elongated support platform member has a concave surface so as to provide a bed for the flaccid penis and the lower side of the elongated support platform member has a convex shape. The adjustable waist-strap is affixed to the oval shaped base and is tightened around a waist of a user. The first and second adjustable leg straps are affixed to the oval-shaped base and are tightened around the thighs of the user so as to secure the prosthetic device against the groin area of the user. The prosthetic device is used in conjunction with a penis extension sleeve.

15 Claims, 5 Drawing Sheets

EXTERNAL PROSTHESIS SYSTEMS

CROSS-REFERENCE TO RELATED APPLICATION

The present application is related to and claims priority from prior provisional application Ser. No. 61/331,920, filed May 6, 2010 which application is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates generally to the field of prosthetic devices and more specifically relates to prosthetic devices used to support a penis during intercourse.

2. Description of the Related Art

Impotence or erectile dysfunction (ED, E.D.) has always been and continues to remain an extremely common disorder. Almost all men experience some level of erectile dysfunction (ED) during their lives. Causes of male impotence include diabetes, high blood pressure, high cholesterol, heart disease, or depression. Further, some medicines that men take for conditions like high blood pressure and depression can lead to ED. Male impotency can have detrimental effects on a man's relationships and on his self-esteem and can lead to psychological difficulties and depression.

In some cases, treatment can involve prescription medication, injections into the penis, a penile prosthesis, a penis pump or vascular reconstructive surgery. Unfortunately, prescription medication or injections in the penis may cause negative side effects, may interact dangerously with other drugs and don't work for everyone. Surgical intervention can be costly and there are some risks involved, such as for instance, infection or bleeding.

Therefore a need exists for an improved prosthetic device used to support a penis during intercourse which affords a man the ability to resume a healthy sex life. A need exists for a prosthetic device which is inexpensive, has no side effects, is easy to use, and which does not require surgery or other costly procedures.

Various attempts have been made to solve the above-mentioned problems such as those found in U.S. Pat. Nos. 5,360,390; 4,653,484; 6,436,031; 4,194,502; D394504; and 3,920,007. This prior art is representative of prosthetic devices. None of the above inventions and patents, taken either singly or in combination, is seen to describe the invention as claimed.

Ideally, a prosthetic device used to support a penis during intercourse should be easy to use, fit comfortably, would operate reliably and be manufactured at a modest expense. Thus, a need exists for a reliable prosthesis system to support a penis during intercourse and to avoid the above-mentioned problems.

BRIEF SUMMARY OF THE INVENTION

In view of the foregoing disadvantages inherent in the known prosthetic devices art, the present invention provides a novel External Prosthesis System. The general purpose of the present invention, which will be described subsequently in greater detail, is to provide a prosthetic device used to support a penis during intercourse.

The prosthetic device disclosed herein preferably comprises the following components: an oval shaped base having an upper end and a lower end, a right side and a left side, and a through-hole; an elongated support platform member having an upper side and a lower side, a front end and a rear end; an adjustable waist-strap; a first adjustable leg strap having a first end and a second end; and a second adjustable leg strap having a first end and a second end.

The through-hole is situated near the upper end of the oval-shaped base and the oval shaped base tapers down such that the lower end forms a rounded off tip. The elongated support platform member extends from the oval-shaped base at a point directly below the through-hole and is orientated at an upward inclined sixty degree angle from the oval shaped base. The upper side of the elongated support platform member has a concave surface so as to provide a bed for a flaccid penis and the lower side of the elongated support platform member has a convex shape.

The adjustable waist-strap is affixed to the right side and to the left side of the oval shaped base at a point proximate the upper end of the oval-shaped base and is tightened around a waist of a user so as to secure the prosthetic device against a groin area of the user. The first end of the first adjustable leg strap is affixed to the right side of the oval-shaped base at a point near the lower end of the oval-shaped base and the second end of the first adjustable leg strap is affixed to the adjustable waist-strap. The first adjustable leg strap is tightened around a right thigh of the user so as to secure the prosthetic device against the groin area of the user. The first end of the second adjustable leg strap is affixed to the left side of the oval shaped base at a point near the lower end of the oval shaped base and the second end of the second adjustable leg strap is affixed to the adjustable waist-strap. The second adjustable leg strap is tightened around a left thigh of the user so as to secure the prosthetic device against the groin area of the user.

The prosthetic device is preferably used in conjunction with a penis extension sleeve which is placed over the flaccid penis and the elongated support platform member (on which the flaccid penis rests) after it is placed through the through-hole. The device thereby assists an impotent user to engage in sexual intercourse.

A kit is also described herein including at least one oval-shaped base having a through-hole, at least one elongated support platform member, at least one adjustable waist-strap, at least one first adjustable leg strap, at least one second adjustable leg strap, and a user instruction manual.

In accordance with the embodiments of the present invention a preferred method of use is disclosed herein comprising: placing a flaccid penis through a through-hole of an oval-shaped base; resting the flaccid penis on an elongated support platform member which is attached to the oval-shaped base; securing an adjustable waist-strap which is attached to the oval-shaped base around a waist of a user; securing a first adjustable leg strap and a second adjustable leg strap which are attached to the oval-shaped base around a right thigh and a left thigh of the user; placing a penis extension sleeve over the flaccid penis resting on the elongated support platform member; performing sexual activity; and taking the prosthetic device off the flaccid penis.

The present invention holds significant improvements and serves as an External Prosthesis System. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, External Prosthesis Systems, constructed and operative according to the teachings of the present invention.

The various embodiments of the present invention will hereinafter be described in conjunction with the appended drawings, wherein like designations denote like elements.

DETAILED DESCRIPTION

As discussed above, embodiments of the present invention relate to a prosthetic device and more particularly to a prosthetic device for supporting a flaccid penis during intercourse.

Figure 1:
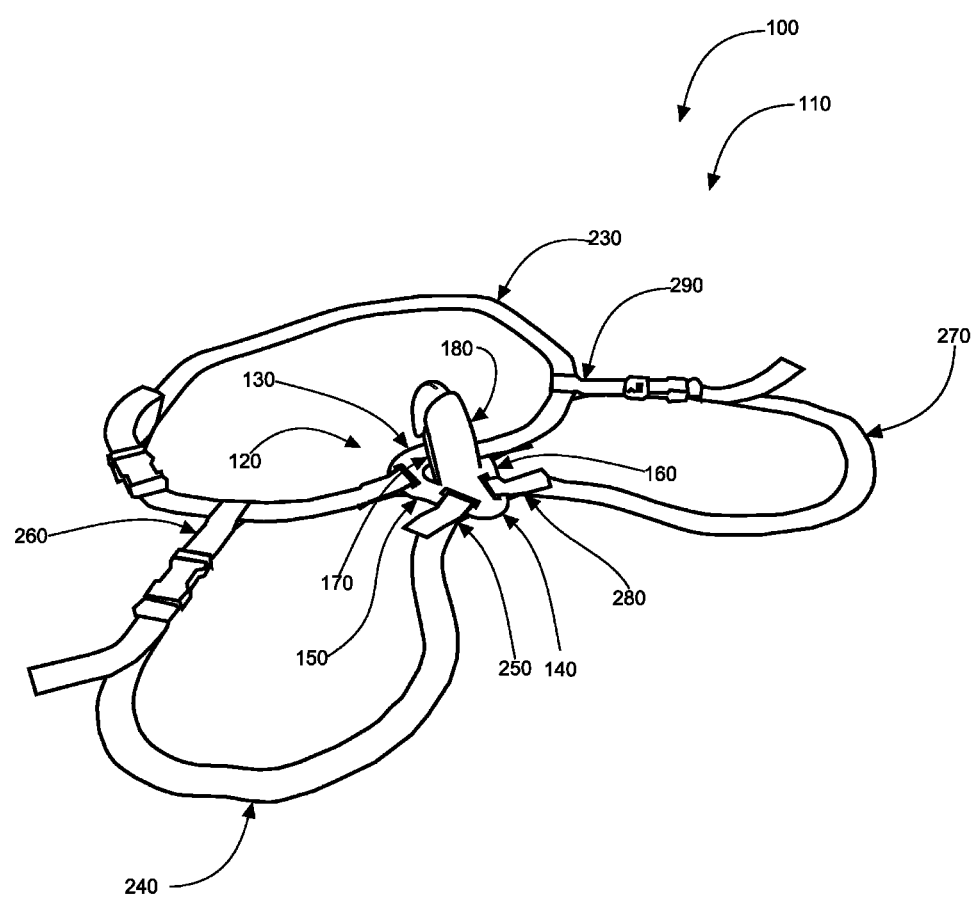
FIG. 1 shows a perspective view illustrating a prosthetic device according to an embodiment of the present invention.

Referring to the drawings by numerals of reference there is shown in FIG. 1, a perspective view illustrating prosthetic device 110 according to an embodiment of the present invention.

External Prosthesis Systems 100 preferably comprises oval shaped base 120 having upper end 130 and lower end 140, right side 150, left side 160, and through-hole 170; elongated support platform member 180 having upper side 190 and lower side 200, front end 210 and rear end 220; adjustable waist-strap 230; first adjustable leg strap 240 having a first end of first adjustable leg strap 250 and a second end of first adjustable leg strap 260; and second adjustable leg strap 270 having a first end of second adjustable leg strap 280 and second end of second adjustable leg strap 290.

Oval shaped base 120 preferably measures 4½ inches in length, 3 inches in width, ¼ inch in depth, and tapers down such that lower end 140 forms a rounded off tip. Through-hole 170 is located at a distance of about ¾ inch below upper end 130 of oval shaped base 120 and at a distance of 1⅞ inches above lower end 140 of oval shaped base 120. Through-hole 170 further is located at a distance of ¾ inch from the edge of right side 150 of oval shaped base 120 and at a distance of ¾ inch from the edge of left side 160 of oval shaped base 120. Through-hole 170 has a diameter of 1⅞ inches to 2 inches.

Oval-shaped base 120 preferably comprises two strap-slots 300 situated near the outer edge of the right side 150 and the left side 160 proximate to the upper end 130 and two strap-slots 300 situated near the outer edge of right side 150 and left side 160 proximate to the lower end 140 of oval shaped base 120. Oval shaped base 120 is preferably made of casting resin. However oval-shaped base 120 may be made of any kind of suitable and durable material, such as putty epoxy or various plastic materials.

Figure 2:
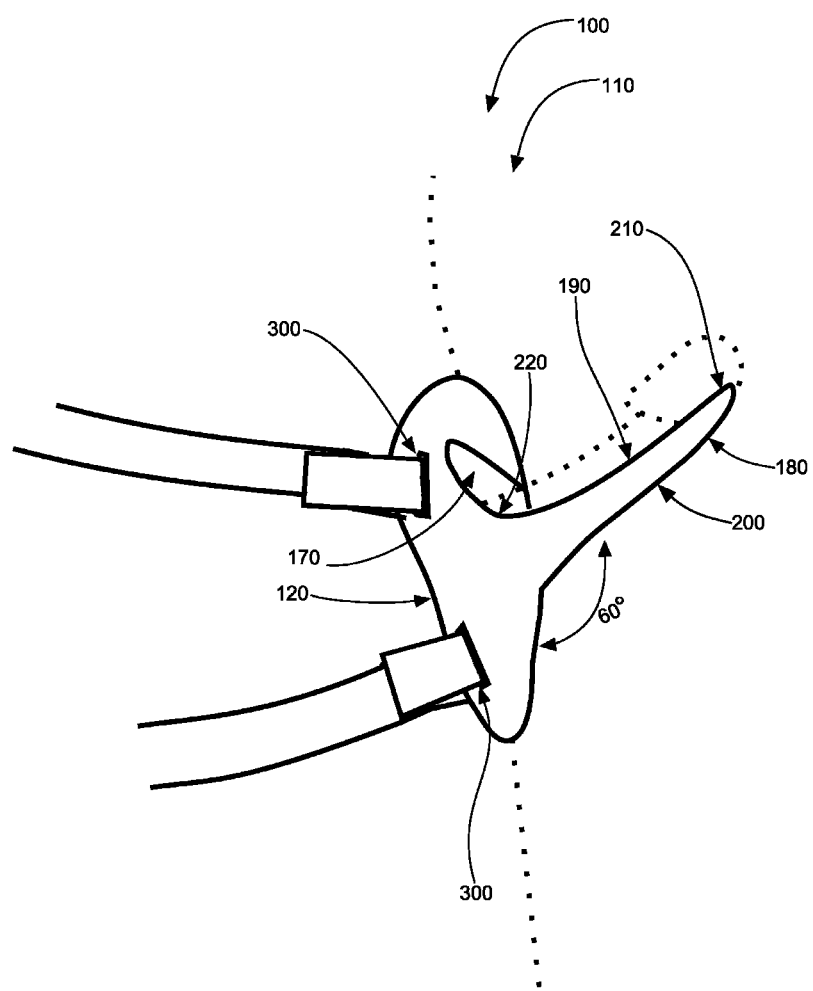
FIG. 2 is a perspective view illustrating the prosthetic device according to an embodiment of the present invention of FIG. 1.

Referring now to FIG. 2, an a perspective view illustrating the prosthetic device 110 according to an embodiment of the present invention of FIG. 1

Elongated support platform member 180 extends from oval-shaped base 120 at a point directly below through-hole 170 and is preferably orientated at an upward inclined sixty degree angle from oval shaped base 120. Oval-shaped base 120 and elongated support platform member 180 preferably are formed in a single-piece construction. Elongated support platform member 180 tapers from a full width of preferably 1½ inches at the rear end 220 to a half width of preferably ¾ inch at the front end 210 and preferably comprises a length of 4 inches (or longer if desired.) In an alternative embodiment, elongated support platform member 180 can be custom-cut to match penis length. Front end 210 of elongated support platform member 180 is preferably rounded off.

Upper side 190 of elongated support platform member 180 preferably comprises a concave surface so as to provide a bed for a flaccid penis. Upper side 190 thereby comprises a groove which makes it easy to keep the flaccid penis rested on upper side 190 of elongated support platform member 180. Lower side 200 of elongated support platform member 180 has a convex shape. Elongated support platform member 180 is preferably made of casting resin. However elongated support platform member 180 may be made of any kind of suitable and durable material such as putty epoxy or various plastic materials. Oval-shaped base 120 and elongated support platform member 180 preferably comprise a smooth surface and smooth rounded-off edges so as to provide a comfort-fit.

Figure 3:
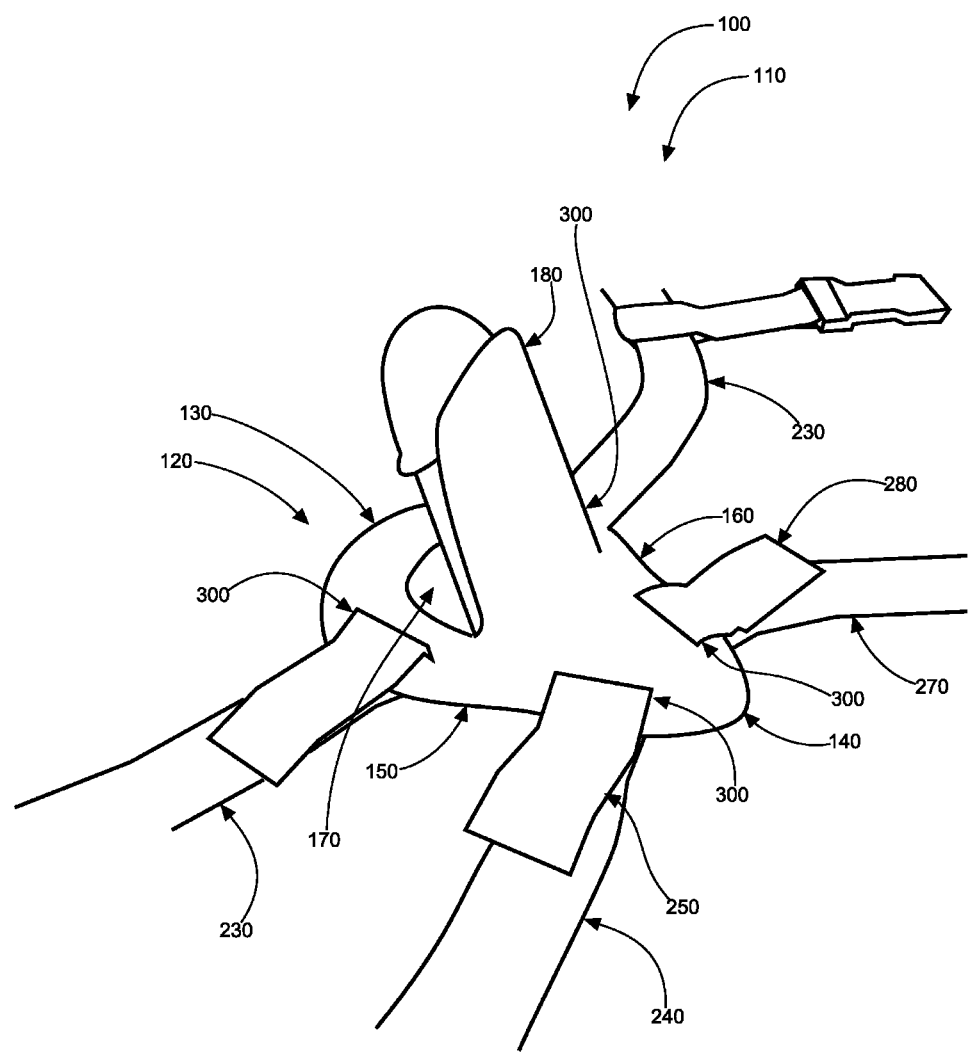
FIG. 3 is a perspective view illustrating the prosthetic device according to an embodiment of the present invention of FIG. 1.
Figure 4:
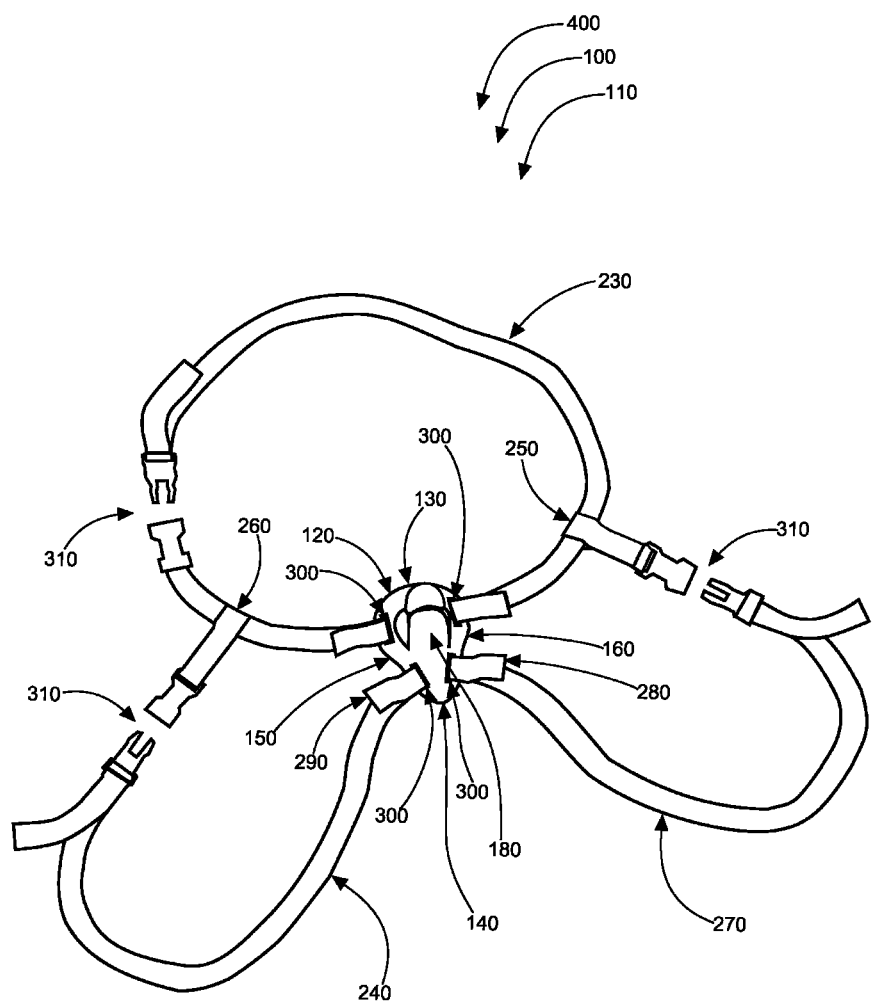
FIG. 4 is a perspective view illustrating the prosthetic device according to an embodiment of the present invention of FIG. 1.

Referring now to FIGS. 3 and 4, perspective views illustrating the prosthetic device 110 according to an embodiment of the present invention of FIG. 1.

Prosthetic device 110 further comprises adjustable waist strap 230, first adjustable leg strap 240 and second adjustable leg strap 270 which preferably are removably attached to oval-shaped base 120.

Adjustable waist-strap 230 is affixed to right side 150 and to left side 160 of oval shaped base 120 at a point proximate upper end 130 of oval-shaped base 120. Adjustable waist-strap 230 is passed through two strap-slots 300 situated on the outer edge of right side 150 and left side 160 of oval shaped base 120 proximate to upper end 130 of oval shaped base 120 and is subsequently affixed to adjustable waist-strap 230 so as to form a loop and thereby connect adjustable waist-strap 230 to oval-shaped base 120. Adjustable waist-strap 230 is tightened around a waist of a user so as to secure prosthetic device 110 against a groin area of the user. Adjustable waist-strap 230 preferably comprises nylon material or braided elastic. However adjustable waist-strap 230 may be made of any kind of suitable and durable material. Adjustable waist-strap 230 preferably comprises a length adjuster 310 so that user can tighten adjustable waist-strap 230 according to his preferences.

First end of first adjustable leg strap 250 is passed through strap-slot 300 which is situated on the outer edge of right side 150 proximate to lower end 140 of oval shaped base 120 and is subsequently affixed to first adjustable leg strap 240 so as to form a loop and connect first adjustable leg strap 240 to oval-shaped base 120. First end of first adjustable leg strap 250 is thereby affixed to the right side 150 of oval-shaped base 120 at a point near lower end 140 of oval-shaped base 120. Second end of first adjustable leg strap 260 is affixed to adjustable waist-strap 230. First adjustable leg strap 240 is tightened around a right thigh of user so as to secure prosthetic device 110 against the groin area of the user.

First end of second adjustable leg strap 280 is passed through strap-slot 300 which is situated on the outer edge of left side 160 proximate to lower end 140 of oval shaped base 120 and is subsequently affixed to second adjustable leg strap 270 so as to form a loop and connect second adjustable leg strap 270 to oval-shaped base 120. First end of second adjustable leg strap 280 is thereby affixed to left side 160 of oval shaped base 120 at a point near lower end 140 of oval shaped base 120. Second end of second adjustable leg strap 290 is affixed to adjustable waist-strap 230. Second adjustable leg strap 270 is tightened around a left thigh of user so as to secure prosthetic device 110 against the groin area of the user.

First adjustable leg strap 240 and second adjustable leg strap 270 preferably comprises braided elastic or of nylon material. However first adjustable leg strap 240 and second adjustable leg strap 270 may be made of any kind of suitable and durable material. First adjustable leg strap 240 and second adjustable leg strap 270 each preferably comprises length adjuster 310 so that user can tighten first adjustable leg strap 240 and second adjustable leg strap 270 according to his preferences.

Prosthetic device 110 is preferably used in conjunction with a penis extension sleeve which is placed over the flaccid penis and the elongated support platform member 180 (on which the flaccid penis rests) after it is placed through through-hole 170. External Prosthesis Systems 100 thereby assists an impotent user to engage in sexual intercourse.

External Prosthesis Systems 100 may be sold as kit 400 comprising the following parts: at least one oval-shaped base 120 having a through-hole 170, at least one elongated support platform member 180, at least one adjustable waist-strap 230, at least one first adjustable leg strap 240, at least one second adjustable leg strap 270, and a user instruction manual.

External Prosthesis Systems 100 may be manufactured and provided for sale in a wide variety of sizes and shapes for a wide assortment of applications. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different color combinations, parts may be sold separately, etc., may be sufficient.

Figure 5:
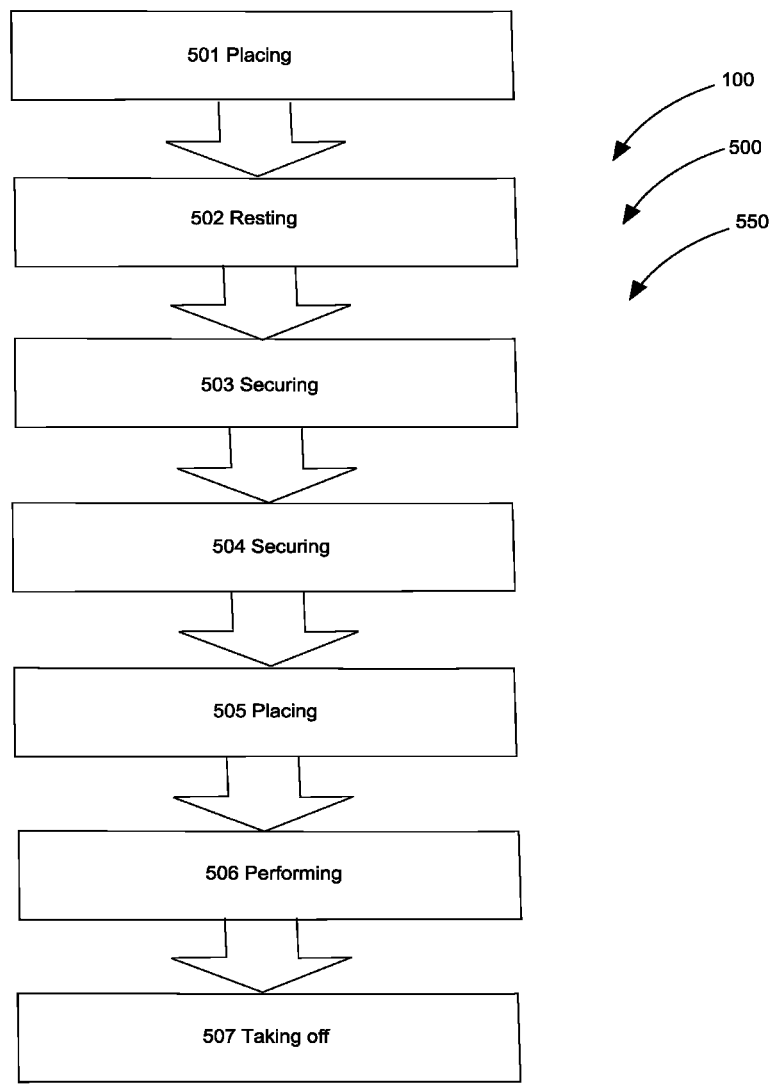
FIG. 5 is a flowchart illustrating a method of use according to an embodiment of the present invention of FIG. 1.

Referring now to FIG. 5, a flowchart 550 illustrating a method of use 500 according to an embodiment of the present invention of FIG. 1.

In accordance with the embodiments of the present invention a preferred method of use 500 is disclosed herein comprising: step one 501 placing a flaccid penis through through-hole 170 of oval-shaped base 120; step two 502 resting the flaccid penis on elongated support platform member 180 which is attached to oval-shaped base 120 (as described above—Prosthetic device 110 is preferably used in conjunction with a penis extension sleeve which is placed over the flaccid penis and the elongated support platform member 180 (on which the flaccid penis rests) after it is placed through through-hole 170); step three 503 securing adjustable waist-strap 230 which is attached to oval-shaped base 120 around a waist of a user; step four 504 securing first adjustable leg strap 240 and second adjustable leg strap 270 which are attached to oval-shaped base 120 around a right thigh and a left thigh of the user; step five placing a penis extension sleeve over the flaccid penis resting on the elongated support platform member 180; step six 506 performing sexual activity; and step seven 507 taking the prosthetic device 110 off the flaccid penis.

It should be noted that the steps described in the method of use 500 can be carried out in many different orders according to user preference. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A prosthetic device for supporting a flaccid penis during intercourse comprising:
   a) an oval shaped base having an upper end and a lower end, a right side and a left side and a through-hole;
   b) an elongated support platform member having an upper side and a lower side, a front end and a rear end;
   c) an adjustable waist-strap;
   d) a first adjustable leg strap having a first end and a second end; and
   e) a second adjustable leg strap having a first end and a second end;
   f) wherein said oval shaped base tapers down such that said lower end forms a rounded off tip of said oval-shaped base;
   g) wherein said through-hole is situated near said upper end of said oval-shaped base;
   h) wherein said elongated support platform member extends from said oval-shaped base at a point directly below said through-hole and said elongated support platform member is orientated at an upward inclined sixty degree angle from said oval shaped base;
   i) wherein said upper side of said elongated support platform member has an concave surface so as to provide a bed for said flaccid penis and said lower side of said elongated support platform member has a convex shape;
   j) wherein said adjustable waist-strap is affixed to said right side and to said left side of said oval shaped base at a point proximate said upper end of said oval-shaped base and is structured and arranged to be tightened around a waist of a user so as to secure said prosthetic device against a groin area of said user;

k) wherein said first end of said first adjustable leg strap is affixed to said right side of said oval-shaped base at a point near said lower end of said oval-shaped base and said second end of said first adjustable leg strap is affixed to said adjustable waist-strap, and said first adjustable leg strap is structured and arranged to be tightened around a right thigh of said user so as to secure said prosthetic device against said groin area of said user;

l) wherein said first end of said second adjustable leg strap is affixed to said left side of said oval shaped base at a point near said lower end of said oval shaped base and said second end of said second adjustable leg strap is affixed to said adjustable waist-strap, and said second adjustable leg strap is structured and arranged to be tightened around a left thigh of said user so as to secure said prosthetic device against said groin area of said user;

m) wherein said adjustable waist strap, said first adjustable leg strap and said second adjustable leg strap are removably attached to said elongated support platform member;

n) wherein said prosthetic device is used in conjunction with a penis extension sleeve which is structured and arranged to be placed over said flaccid penis after it is placed through said through-hole and while said flaccid penis rests on said elongated support platform member; and o) wherein said prosthetic device assists an impotent said user to engage in sexual intercourse.

2. The prosthetic device of claim 1 wherein said oval-shaped base and said elongated support platform member are formed in a single-piece construction.

3. The prosthetic device of claim 1 wherein said oval-shaped base and said elongated support platform member comprise casting resin.

4. The prosthetic device of claim 1 wherein said oval-shaped base and said elongated support platform member comprise putty epoxy.

5. The prosthetic device of claim 1 wherein said oval-shaped base and said elongated support platform member comprise plastic.

6. The prosthetic device of claim 1 wherein said oval-shaped base comprises two upper strap-slots situated on an upper outer edge of said right side and on an upper outer edge of said left side proximate to said upper end and two lower strap-slots situated on a lower outer edge of said right side and on a lower outer edge of said left side proximate to said lower end.

7. The prosthetic device of claim 1 wherein said elongated support platform member tapers from a full width at said rear end to a half width at said front end.

8. The prosthetic device of claim 1 wherein said support platform member can be custom-cut to penis length.

9. The prosthetic device of claim 1 wherein said front end of said elongated support platform member is rounded.

10. The prosthetic device of claim 1 wherein said oval-shaped base and said elongated support platform member comprise a smooth surface and smooth rounded-off edges so as to provide a comfort-fit.

11. The prosthetic device of claim 1 wherein said adjustable waist-strap, said first adjustable leg strap and said second adjustable leg strap comprise length adjusters.

12. The prosthetic device of claim 1 wherein said adjustable waist-strap, said first adjustable leg strap and said second adjustable leg strap comprise braided elastic.

13. A method of using a prosthetic device of claim 1 for supporting a flaccid penis during intercourse comprising the steps of:

a) placing said flaccid penis through said through-hole of said oval-shaped base;

b) resting said flaccid penis on said elongated support platform member which is attached to said oval-shaped base and donning said penis extension sleeve over said flaccid penis and said elongated support platform member;

c) securing said adjustable waist-strap which is attached to said oval-shaped base around said waist of said user;

d) securing said first adjustable leg strap and said second adjustable leg strap which are attached to said oval-shaped base around said right thigh and said left thigh of said user;

e) placing said penis extension sleeve over said flaccid penis resting on said elongated support platform member;

f) performing sexual activity; and g) taking said prosthetic device off said flaccid penis.

14. A prosthetic device for supporting a flaccid penis during intercourse comprising:

a) an oval shaped base made of casting resin and having an upper end and a lower end, a right side and a left side and a through-hole;

b) an elongated support platform member made of casting resin and having an upper side and a lower side, a rounded front end and a rear end;

c) an adjustable waist-strap comprising a length adjuster;

d) a first adjustable leg strap comprising a length adjuster, a first end, and a second end; and e) a second adjustable leg strap comprising a length adjuster, a first end, and a second end;

f) wherein said oval shaped base tapers down such that said lower end forms a rounded off tip of said oval-shaped base;

g) wherein said oval-shaped base comprises two upper strap-slots situated on an upper outer edge of said right side and on an upper outer edge of said left side proximate to said upper end and two lower strap-slots situated on a lower outer edge of said right side and on a lower outer edge of said left side proximate to said lower end;

h) wherein said through-hole is situated near said upper end of said oval-shaped base;

i) wherein said elongated support platform member extends from said oval-shaped base at a point directly below said through-hole and said elongated support platform member is orientated at an upward inclined sixty degree angle from said oval shaped base;

j) wherein said upper side of said elongated support platform member has a concave surface so as to provide a bed for said flaccid penis and said lower side of said elongated support platform member has a convex shape;

k) wherein said elongated support platform member tapers from a full width at said rear end to a half width at said front end;

l) wherein said oval-shaped base and said elongated support platform member are formed in a single-piece construction and comprise a smooth surface and smooth rounded-off edges so as to provide a comfort-fit;

m) wherein said adjustable waist-strap is removably attached to said right side and to said left side of said oval shaped base at a point proximate said upper end of said oval-shaped base and is structured and arranged to be tightened around a waist of a user so as to secure said prosthetic device against a groin area of said user;

n) wherein said first end of said first adjustable leg strap is removably attached to said right side of said oval-shaped base at a point near said lower end of said oval-shaped base and said second end of said first adjustable leg strap is affixed to said adjustable waist-strap, and said first adjustable leg strap is structured and arranged to be tightened around a right thigh of said user so as to secure said prosthetic device against said groin area of said user;

o) wherein said first end of said second adjustable leg strap is removably attached to said left side of said oval shaped base at a point near said lower end of said oval shaped base and said second end of said second adjustable leg strap is affixed to said adjustable waist-strap, and said second adjustable leg strap is structured and arranged to be tightened around a left thigh of said user so as to secure said prosthetic device against said groin area of said user;

p) wherein said adjustable waist strap, said first adjustable leg strap and said second adjustable leg strap are removably attached to said elongated support platform member;

q) wherein said prosthetic device is used in conjunction with a penis extension sleeve which is structured and arranged to be placed over said flaccid penis after it is placed through said through-hole and while said flaccid penis rests on said elongated support platform member; and wherein said prosthetic device assists an impotent said user to engage in sexual intercourse.

15. The prosthetic device of claim 14 further comprising a kit including said at least one oval-shaped base having said through-hole, said at least one elongated support platform member, said at least one adjustable waist-strap, said at least one first adjustable leg strap, said at least one second adjustable leg strap, and a user instruction manual.

* * * * *